US00PP34587P2

(12) United States Plant Patent
Koot

(10) Patent No.: US PP34,587 P2
(45) Date of Patent: Sep. 13, 2022

(54) ***CALIBRACHOA* PLANT NAMED 'DOCALRAIORO'**

(50) Latin Name: *Calibrachoa parviflora*
Varietal Denomination: 'Docalraioro'

(71) Applicant: DUMMEN GROUP B.V., De Lier (NL)

(72) Inventor: Arjan Koot, Oeffelt (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/698,723

(22) Filed: Mar. 18, 2022

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. Anne Whealy

(57) ABSTRACT

A new and distinct cultivar of *Calibrachoa* plant named 'Docalraioro', characterized by its outwardly spreading, trailing and decumbent plant habit; moderately vigorous growth habit and moderate growth rate; freely branching habit; early and freely flowering habit; large flowers with light red-colored petals with yellow-colored centers; and good container and garden performance.

2 Drawing Sheets

Figure 1:
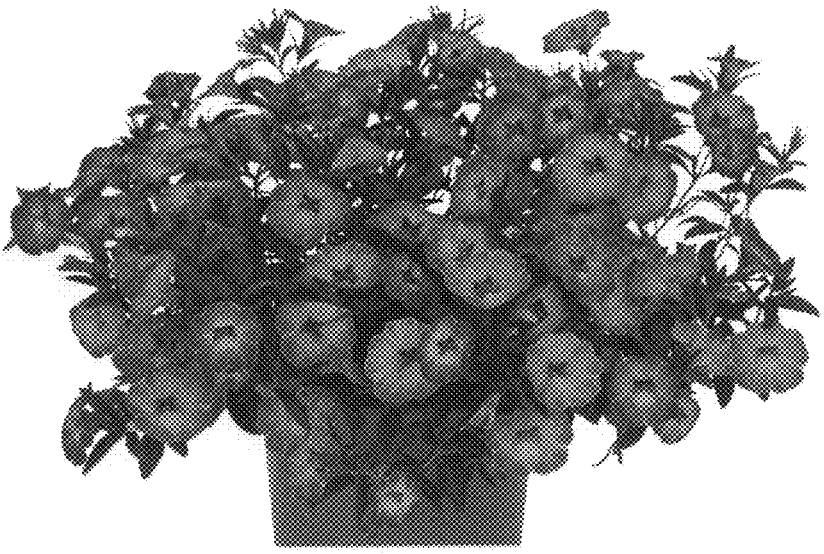

Botanical designation: *Calibrachoa parviflora.*
Cultivar denomination: 'DOCALRAIORO'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Calibrachoa* plant, botanically known as *Calibrachoa parviflora* and hereinafter referred to by the name 'Docalraioro'.

The new *Calibrachoa* plant is a product of a planned breeding program conducted by the Inventor in Rheinberg, Germany. The objective of the breeding program is to create new freely branching and early-flowering *Calibrachoa* plants with numerous large and attractive flowers.

The new *Calibrachoa* plant originated from a cross-pollination made by the Inventor in July, 2019 in Rheinberg, Germany of a proprietary selection of *Calibrachoa parviflora* identified as code number AA19-K0048, not patented, as the female, or seed, parent with a proprietary selection of *Calibrachoa parviflora* identified as code number AA19-K0249, not patented, as the male, or pollen, parent. The new *Calibrachoa* plant was discovered and selected by the Inventor as a single flowering plant from within the progeny of the stated cross-pollination in a controlled greenhouse environment in Rheinberg, Germany in May, 2021.

Asexual reproduction of the new *Calibrachoa* plant by vegetative terminal cuttings in a controlled greenhouse environment in Rheinberg, Germany since June, 2021 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Docalraioro'. These characteristics in combination distinguish 'Docalraioro' as a new and distinct *Calibrachoa* plant:

1. Outwardly spreading, trailing and decumbent plant habit.
2. Moderately vigorous growth habit and moderate growth rate.
3. Freely branching habit.
4. Early and freely flowering habit.
5. Large flowers with light red-colored petals with yellow-colored centers.
6. Good container and garden performance.

The new *Calibrachoa* can be compared to plants of the female parent selection. Plants of the new *Calibrachoa* differ primarily from plants of the female parent selection in flower color as plants of the new *Calibrachoa* have light red-colored flowers with yellow-colored centers whereas plants of the female parent selection have red-colored flowers. In addition, plants of the new *Calibrachoa* are more vigorous than plants of the female parent selection.

The new *Calibrachoa* can be compared to plants of the male parent selection. Plants of the new *Calibrachoa* differ primarily from plants of the male parent selection in flower color as plants of the new *Calibrachoa* have more yellow-colored flower centers than plants of the male parent selection. In addition, plants of the new *Calibrachoa* have larger flowers than plants of the male parent selection.

Plants of the new *Calibrachoa* can also be compared to plants of *Calibrachoa* sp. 'Wescachasube', not patented. In side-by-side comparisons, plants of the new *Calibrachoa* differ primarily from plants of 'Wescachasube' in the following characteristics:

1. Plants of the new *Calibrachoa* are more freely flowering than plants of 'Wescachasube'.
2. Plants of the new *Calibrachoa* have larger flowers than plants of 'Wescachasube'.
3. Plants of the new *Calibrachoa* have light red-colored flowers with yellow-colored centers whereas plants of 'Wescachasube' have deep purplish red-colored flowers with yellow-colored centers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'Docalraioro' grown in a container.

Figure 2:
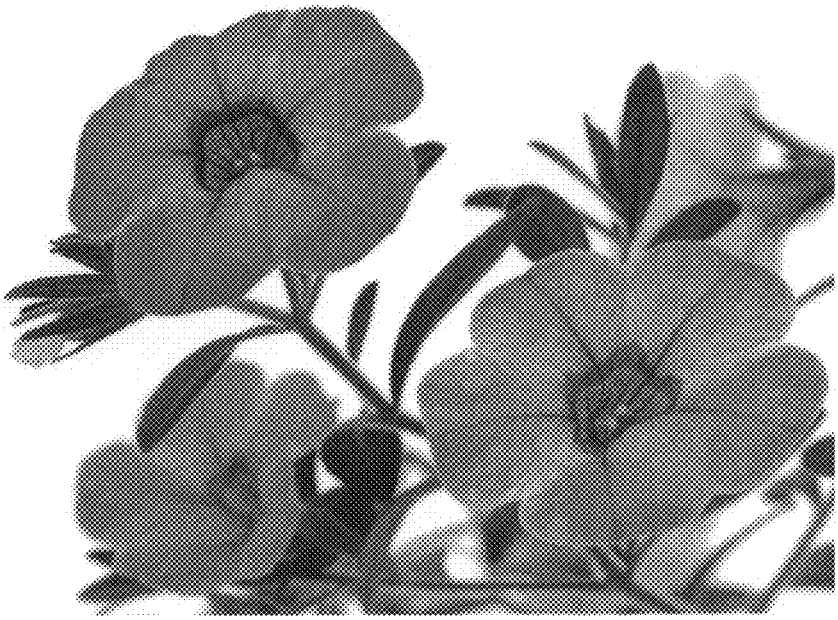

The photograph on the second sheet (FIG. 2) is a close-up view of a typical flowering plant of 'Docalraioro'.

DETAILED BOTANICAL DESCRIPTION

The aforementioned photographs and following observations, measurements and values describe plants grown during the spring and early summer in 22-cm containers in a glass-covered greenhouse in Rheinberg, Germany and under cultural practices typical of commercial *Calibrachoa* production. During the production of the plants, day and night temperatures averaged 18° C. and light levels averaged 4,500 lux. Rooted young plants were pinched one time three weeks after planting. Plants were twelve weeks old when the photographs were taken and 25 weeks old when the description was taken. In the following description, color references are made to The Royal Horticultural Society Colour Chart, Fifth Edition, except where general terms of ordinary dictionary significance are used.

Botanical classification: *Calibrachoa parviflora* 'Docalraioro'.

Parentage:

*Female, or seed, parent*.—Proprietary selection of *Calibrachoa parviflora* identified as code number AA19-K0048, not patented.

*Male, or pollen, parent*.—Proprietary selection of *Calibrachoa parviflora* identified as code number AA19-K0249, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Outwardly spreading to trailing and decumbent plant habit; freely branching habit with about six primary lateral branches each with about 14 secondary lateral branches developing per plant; pinching enhances branching; dense and full appearance; moderately vigorous growth habit and moderate growth rate.

*Plant height, soil level to top of foliar plane*.—About 18 cm.

*Plant height, soil level to top of floral plane*.—About 21.5 cm.

*Plant diameter* (*spread of plant*).—About 68.5 cm.

Lateral branch description:

*Length*.—About 41 cm.

*Diameter*.—About 5 mm.

*Internode length*.—About 1.7 cm.

*Strength*.—Strong.

*Aspect*.—Initially upright to outwardly spreading to trailing and decumbent.

*Texture and luster*.—Pubescent; glossy.

*Color, developing*.—Close to 143C.

*Color, developed*.—Close to 146C.

Leaf description:

*Arrangement*.—Before flowering, alternate, and after flowering, opposite; simple.

*Length*.—About 2.9 cm.

*Width*.—About 7 mm.

*Shape*.—Oblanceolate.

*Apex*.—Rounded.

*Base*.—Attenuate.

*Margin*.—Entire.

*Texture and luster, upper and lower surfaces*.—Pubescent; matte.

*Venation pattern*.—Pinnate; arcuate.

*Color*.—Developing leaves, upper surface: Close to 143A. Developing leaves, lower surface: Close to 137C. Fully expanded leaves, upper surface: Close to 137A; venation, close to 144C. Fully expanded leaves, lower surface: Close to 137C; venation, close to 144D.

*Petioles*.—Length: About 3.2 mm. Diameter: About 1.3 mm. Strength: Moderately strong. Texture and luster, upper and lower surfaces: Pubescent; matte. Color, upper surface: Close to 144A. Color, lower surface: Close to 144C.

Flower description:

*Flower arrangement and habit*.—Single salverform flowers arising from leaf axils; freely flowering habit with usually about 612 flowers and flower buds developing per plant; flowers face mostly upright to outwardly.

*Fragrance*.—None detected.

*Natural flowering season*.—Early flowering habit, plants of the new *Calibrachoa* initiate and develop flowers about six weeks after planting; plants flower continuously from the spring throughout the summer in Germany.

*Flower longevity*.—Individual flowers last about seven to ten days on the plant; flowers not persistent.

*Flower buds*.—Length: About 2.6 cm. Diameter: About 4.8 mm. Shape: Elongated oblong. Texture and luster: Rippled; semi-glossy. Color: Close to 150B and 63A.

*Flower diameter*.—About 3.3 cm by 3.4 cm.

*Flower depth* (*height*).—About 3.2 cm.

*Flower throat diameter*.—About 7.8 mm.

*Flower tube length*.—About 1.8 cm.

*Flower tube diameter*.—About 8.9 mm.

*Corolla*.—Arrangement: Five petals fused at the base and opening into a flared trumpet. Petal length from throat: About 1.7 cm. Petal lobe width: About 1.9 cm. Petal shape: Roughly spatulate. Petal apex: Rounded. Petal margin: Entire; slightly undulate. Petal texture and luster, upper and lower surfaces: Smooth, glabrous; matte. Throat texture: Smooth, glabrous. Tube texture: Smooth, glabrous. Color: Petal, when opening, upper surface: Close to 50A to 50B; center, close to 6A. Petal, when opening, lower surface: Close to 63B. Petal, fully opened, upper surface: Close to 51A; center, close to 6A; venation, close to 50A and 167A; color becoming closer to 39A and center, close to 6B, with subsequent development. Petal, fully opened, lower surface: Close to 51B; venation, close to 149A and 51B; color becoming closer to 51C with subsequent development. Throat: Close to 6A and N34A; venation, close to 152A. Tube: Close to 1B; venation, close to N144B.

*Calyx*.—Arrangement: Star-shaped calyx with five sepals; sepals fused at the base. Sepal length: About 1 cm. Sepal width: About 2.7 mm. Sepal shape: Lanceolate. Sepal apex: Acute. Sepal margin: Entire. Sepal texture and luster, upper and lower surfaces: Pubescent; matte. Color: When developing and fully developed, upper surface: Close to 137B. When developing and fully developed, lower surface: Close to 137C.

*Peduncles*.—Length: About 1.2 cm. Diameter: About 1 mm. Angle: About 45° from stein axis. Strength: Moderately strong. Texture and luster: Pubescent; matte. Color: Close to 144C.

*Reproductive organs*.—Stamens: Quantity: Five per flower. Filament length: About 1 cm. Filament color: Close to 145C. Anther length: About 1 mm. Anther shape: Ellipsoidal. Anther color: Close to 4C. Pollen amount: Scarce. Pollen color: Close to 14C. Pistils: Quantity: One per flower. Pistil length: About 1.2 cm. Style length: About 8 mm. Style color: Close to 144D. Stigma diameter: About 0.8 mm. Stigma shape: Ellipsoidal. Stigma color: Close to 144C. Ovary color: Close to 144C. Fruits: Quantity produced per plant: About 960 per plant. Length: About 6 mm. Diameter: About 3.5 mm. Texture: Smooth, glabrous. Color: Close to N199D. Seeds: Quantity per flower: About 55. Length: About 1 mm. Diameter: About 1 mm. Texture: Smooth, glabrous. Color: Close to 202A.

Garden performance: Plants of the new *Calibrachoa* have been observed to have good garden performance and to tolerate wind, rain, temperatures ranging from about 5° C. to about 40° C. and to be suitable for USDA Hardiness Zone 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'Docalraioro' as illustrated and described.

* * * * *